United States Patent
Fan et al.

(10) Patent No.: US 12,194,124 B2
(45) Date of Patent: Jan. 14, 2025

(54) PERSONAL CARE COMPOSITIONS FOR TREATING ODOR CAUSING BACTERIA AND METHODS FOR THE SAME

(71) Applicant: Colgate-Palmolive Company, New York, NY (US)

(72) Inventors: Aixing Fan, Bridgewater, NJ (US); Min Li, Bridgewater, NJ (US); Thomas Boyd, Metuchen, NJ (US); Shyamala Pillai, Hillsborough, NJ (US); Katie Truong, Piscataway, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/658,288

(22) Filed: Apr. 7, 2022

(65) Prior Publication Data
US 2022/0241162 A1 Aug. 4, 2022

Related U.S. Application Data

(63) Continuation of application No. 16/684,330, filed on Nov. 14, 2019, now Pat. No. 11,331,253.

(51) Int. Cl.
| | | |
|---|---|---|
| *A61K 8/34* | (2006.01) | |
| *A61K 8/20* | (2006.01) | |
| *A61K 8/27* | (2006.01) | |
| *A61K 8/37* | (2006.01) | |
| *A61K 8/41* | (2006.01) | |
| *A61K 8/42* | (2006.01) | |
| *A61K 8/49* | (2006.01) | |
| *A61K 8/86* | (2006.01) | |
| *A61Q 15/00* | (2006.01) | |
| *A61Q 17/00* | (2006.01) | |

(52) U.S. Cl.
CPC ............... *A61K 8/342* (2013.01); *A61K 8/20* (2013.01); *A61K 8/27* (2013.01); *A61K 8/345* (2013.01); *A61K 8/37* (2013.01); *A61K 8/41* (2013.01); *A61K 8/416* (2013.01); *A61K 8/42* (2013.01); *A61K 8/4926* (2013.01); *A61K 8/86* (2013.01); *A61Q 15/00* (2013.01); *A61Q 17/005* (2013.01)

(58) Field of Classification Search
CPC ....... A61K 8/342; A61Q 15/00; A61Q 17/005
See application file for complete search history.

(56) References Cited

U.S. PATENT DOCUMENTS

| | | |
|---|---|---|
| 2,350,047 A | 5/1944 | Emil et al. |
| 5,262,153 A | 11/1993 | Mishima et al. |
| 5,618,522 A | 4/1997 | Deckner et al. |
| 5,785,962 A | 7/1998 | Hinz et al. |
| 6,017,548 A | 1/2000 | Epstein et al. |
| 6,139,850 A | 10/2000 | Hahn et al. |
| 6,365,137 B1 | 4/2002 | Aust et al. |
| 7,250,174 B2 | 7/2007 | Lee et al. |
| 8,227,426 B2 | 7/2012 | Gupta et al. |
| 8,741,357 B2 | 6/2014 | Lamy et al. |
| 8,802,065 B2 | 8/2014 | Oshimura et al. |
| 8,933,131 B2 | 1/2015 | Carter et al. |
| 8,992,898 B2 | 3/2015 | Klingman |
| 9,566,223 B2 | 2/2017 | Klingman |
| 9,713,604 B2 | 7/2017 | Dreher |
| 10,071,103 B2 | 9/2018 | Sengupta et al. |
| 10,406,085 B2 | 9/2019 | Dubovoy et al. |
| 10,532,014 B2 | 1/2020 | Lesniak et al. |
| 10,561,593 B2 | 2/2020 | Wu |
| 10,638,755 B2 | 5/2020 | Pesaro et al. |
| 10,864,147 B2 | 12/2020 | Hilliard, Jr. et al. |
| 10,933,000 B2 | 3/2021 | Hilliard, Jr. et al. |
| 11,090,249 B2 | 8/2021 | Mitchell et al. |
| 11,104,868 B2 | 8/2021 | Hardy et al. |
| 2003/0053970 A1* | 3/2003 | Bruening ............ A61K 8/39 424/68 |
| 2004/0076654 A1 | 4/2004 | Vinson et al. |
| 2006/0182708 A1 | 8/2006 | Bockmuhl et al. |
| 2007/0167529 A1 | 7/2007 | Walton et al. |
| 2007/0243155 A1 | 10/2007 | Bottiglieri et al. |

(Continued)

FOREIGN PATENT DOCUMENTS

| | | |
|---|---|---|
| CN | 101107045 | 1/2008 |
| CN | 101182299 | 5/2008 |
| CN | 101820753 | 9/2010 |
| CN | 103690380 | 4/2014 |
| CN | 109259188 | 1/2019 |
| DE | 19643585 | 4/1998 |
| DE | 102004032734 | 10/2005 |
| EP | 0345082 | 12/1989 |
| EP | 0749749 | 12/1996 |
| EP | 1443892 | 8/2004 |
| EP | 1510200 | 3/2005 |

(Continued)

OTHER PUBLICATIONS

Boyd (https://www.chemservice.com/news/2014/08/which-chemicals-make-deodorants-and-antiperspirants-work/), Aug. 22, 2014, pp. 1-2 (Year:2014).

(Continued)

*Primary Examiner* — Andrew S Rosenthal

(57) ABSTRACT

Compositions, such as personal care compositions, and methods for selectively inhibiting the growth of a detrimental bacteria and promoting the growth of a beneficial bacteria are disclosed. The composition may include a base and one or more fatty alcohols. The one or more fatty alcohols may be present in an amount effective to selectively inhibit the growth of at least one detrimental Gram-positive bacteria and promote the growth of at least one beneficial Gram-positive bacteria on skin. The detrimental Gram-positive bacteria may include *Corynebacterium*, and the beneficial Gram-positive bacteria may include *Staphylococcus*.

13 Claims, No Drawings

(56) References Cited

U.S. PATENT DOCUMENTS

| | | | |
|---|---|---|---|
| 2008/0187562 A1* | 8/2008 | Fan | A61Q 15/00 424/401 |
| 2008/0206170 A1 | 8/2008 | Nivaggioli et al. | |
| 2008/0299068 A1 | 12/2008 | Omura et al. | |
| 2010/0160242 A1* | 6/2010 | Masui | A61L 9/01 514/561 |
| 2010/0189753 A1 | 7/2010 | Van Bavel et al. | |
| 2011/0212144 A1* | 9/2011 | Lemoine | A61K 8/45 424/401 |
| 2012/0006348 A1 | 1/2012 | Grollier et al. | |
| 2013/0059929 A1 | 3/2013 | Koehler et al. | |
| 2014/0205555 A1 | 7/2014 | Gale et al. | |
| 2015/0050227 A1 | 2/2015 | Liu et al. | |
| 2015/0202136 A1 | 7/2015 | Lanzalaco et al. | |
| 2016/0151257 A1 | 6/2016 | Klingman | |
| 2017/0183452 A1 | 6/2017 | Panandiker et al. | |
| 2018/0177692 A1* | 6/2018 | Garcia | A61K 8/86 |
| 2019/0183780 A1 | 6/2019 | Pan et al. | |
| 2019/0270951 A1 | 9/2019 | Hardy et al. | |
| 2020/0016053 A1 | 1/2020 | Hilliard, Jr. et al. | |
| 2020/0405674 A1 | 12/2020 | Schiller et al. | |
| 2021/0275418 A1 | 9/2021 | Bhardwaj | |
| 2021/0283025 A1 | 9/2021 | Das et al. | |
| 2021/0299020 A1 | 9/2021 | Cruz et al. | |
| 2022/0031591 A1 | 2/2022 | Botto et al. | |
| 2022/0079854 A1 | 3/2022 | Li et al. | |
| 2022/0241162 A1 | 8/2022 | Fan et al. | |
| 2022/0395437 A1 | 12/2022 | Leva | |
| 2023/0082090 A1 | 3/2023 | Guzman et al. | |

FOREIGN PATENT DOCUMENTS

| | | | |
|---|---|---|---|
| EP | 1526827 | 5/2005 | |
| EP | 2353579 | 8/2011 | |
| EP | 2353579 A1 * | 8/2011 | A61K 8/342 |
| EP | 2374835 | 10/2011 | |
| JP | H09110650 | 4/1997 | |
| JP | 2004-089177 | 3/2004 | |
| KR | 20120070104 | 6/2012 | |
| KR | 101189187 | 10/2012 | |
| KR | 20140039548 | 4/2014 | |
| KR | 20150011060 | 1/2015 | |
| KR | 101503979 | 3/2015 | |
| KR | 101768921 | 8/2017 | |
| WO | 2009/020582 | 2/2009 | |
| WO | 2009/046008 | 4/2009 | |
| WO | 2010/044076 | 4/2010 | |
| WO | 2011/099849 | 8/2011 | |
| WO | 2017/030560 | 2/2017 | |
| WO | 2018/022016 | 2/2018 | |
| WO | 2019/117858 | 6/2019 | |
| WO | 2020/052916 | 3/2020 | |
| WO | 2020/057761 | 3/2020 | |
| WO | 2020/185654 | 9/2020 | |
| WO | 2021/096518 | 5/2021 | |
| WO | 2021/183462 | 9/2021 | |
| WO | 2021/183464 | 9/2021 | |
| WO | 2022/063857 | 3/2022 | |
| WO | 2023/034493 | 3/2023 | |

OTHER PUBLICATIONS

International Search Report and the Written Opinion of the International Searching Authority issued in International Application PCT/US2019/061522 mailed May 12, 2020.
Allies Group, 2017, "Promise Keeper Blemish Facial", Mintel Database GNPD AN: 5196555.
Anonymous, "Ingredients of Filorga Ultimate Revitalizing Night Cream," retrieved from https://www.cosdna.com/chs/cosmetic_4251189624.html, published on May 16, 2015.
Institut Esthederm, 2011, "E.V.E. Essential Vital Elements Serum Source", Mintel Database GNPD AN: 1666406.
Briseis, 2005, "Intensity Classic Deo Roll-On", Mintel Database GNPD AN: 371579.
Coop, 2014, "Intimate Wash", Mintel Database GNPD AN: 2677521.
Dr. Dennis Gross Skincare, 2014, "Clinical Concentrate Radiance Booster", Mintel Database GNPD AN: 2350479.
Glamglow, 2012, "Super-Mud Clearing Treatment", Mintel Database GNPD AN: 1921209.
Glamglow, 2019, "Superserum 6-Acid Refining Treatment", Mintel Database GNPD AN: 6521601.
Glamglow, 2019, "Supertoner Exfoliating Acid Soution", Mintel Database GNPD AN: 6457009.
International Search Report and the Written Opinion of the International Searching Authority issued in International Application PCT/US2020/021657 mailed May 27, 2020.
International Search Report and the Written Opinion of the International Searching Authority issued in International Application PCT/US2021/021426 mailed Jun. 28, 2021.
International Search Report and the Written Opinion of the International Searching Authority issued in International Application PCT/US2021/021428 mailed Jun. 28, 2021.
Johnson & Johnson, 2006, "Micro Exfoliating Oxygenating Gel", Mintel Database GNPD AN: 598917.
Novartis Consumer Health, 2011, "Milk Body Lotion", Mintel Database GNPD AN: 1632704.
Personal Collection, 2018, "Shaveless Hair Minimizing Anti-Perspirant Deodorant Roll-On", Mintel Database GNPD AN: 5574907.
Skin Design London, 2017, "Acne On The Spot Serum", Mintel Database GNPD AN: 4688909.
WPI Thomson Database An: 2019-11530B and CN 109259188.
IFSCC, 1998, Antiperspirants-and-Deodorants: Principles of Underarm Technology, Micelle press IFSCC No. 6, pp. 1-61.
Colgate-Palmolive, 2021, "Atopicare Shower Cream", Mintel Database GNPD AN: 8747223.
Evans et al., 2012, "Axillary skin biology and care", International Journal of Cosmetic Science, 34:389-395.
International Search Report and the Written Opinion of the International Searching Authority issued in International Application PCT/US2022/042327 mailed Dec. 20, 2022.
International Search Report and the Written Opinion of the International Searching Authority issued in International Application PCT/US2022/042563 mailed Jan. 20, 2023.
Laboratoire SVR, 2017, "48H Anti-Perspirant Deodorant Roll-on", Mintel Database GNPD AN: 5111953.
Johnson, 2022, "How to Best Treat Acne Scars," Medical News Today (online website: [(https://www.medicalnewstoday.com/articles/324784, pp. 1-14)].
Celltrion Skincure, 2021, "Cleansing Oil & Blackhead", Mintel Database GNPD AN: 8549187.
Coreana Cosmetics, 2020, "Peeling Pad", Mintel Database GNPD AN: 7440987.
International Search Report and the Written Opinion of the International Searching Authority issued in International Application PCT/US2023/084725 mailed Mar. 28, 2024.
Cork, 1996, "The role of *Staphylococcus aureus* in atopic eczema: treatment strategies", Journal of the European Academy of Dermatology and Venereology, vol. 7, Suppl. 1, pp. 31-37.
Cosinter, 2011, "Intimate Liquid Soap", Mintel Database GNPD AN: 1547745.
Do Couto et al., 2016, "Antifungal Activity of the Piroctone Olamine in Intra-Abdominal Candidiasis", Spinger Plus, 5:468.
International Search Report and the Written Opinion of the International Searching Authority issued in International Application PCT/US2023/031519 mailed Nov. 30, 2023.
International Search Report and the Written Opinion of the International Searching Authority issued in International Application PCT/US2023/031632 mailed Nov. 30, 2023.
Patel, 2014, "Postinflammatory hyperpigmentation: Review of pathogenesis, prevention, and treatment", Pigment International, vol. 1, Issue 2, pp. 59-69.
Pharma Solutions, 2022, "Cleansing Bar", Mintel Database GNPD AN: 9713532.

* cited by examiner

PERSONAL CARE COMPOSITIONS FOR TREATING ODOR CAUSING BACTERIA AND METHODS FOR THE SAME

BACKGROUND

Personal care compositions, such as antiperspirant/deodorant compositions, are often used to reduce the perspiration in an axillary (underarm) region and to treat or prevent the growth of bacteria in this region to thereby reduce or eliminate body odor. There is a wide array of bacteria that reside on our skin, especially in the axillary region. The most common bacterial genus on our skin is *Staphylococcus* bacteria, which includes *Staphylococcus epidermidis*, one of the most studied and known microbes. *Staphylococcus epidermidis* is a beneficial bacteria. Specifically, it produces antimicrobial peptides (AMP) and provides a barrier against the colonization of potentially pathogenic microbes and the overgrowth of opportunistic pathogens. While some bacteria, such as *Staphylococcus epidermidis*, have demonstrated some benefits to skin, other bacteria, such as Corynebacteria have proven to be undesirable. For example, there is ample evidence to indicate that Corynebacteria (Coryneforms) are the primary source of undesired, pungent underarm odors.

What is needed, then, are improved personal care compositions, such as antiperspirant/deodorant compositions, that selectively inhibit, treat, or reduce the growth of detrimental bacteria, such as Corynebacteria, and/or promote the growth of beneficial bacteria, such as *Staphylococcus epidermidis*.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a composition including a base and one or more fatty alcohols. The one or more fatty alcohols may be present in an amount effective to selectively inhibit the growth of at least one detrimental Gram-positive bacteria and promote the growth of at least one beneficial Gram-positive bacteria on skin.

In at least one implementation, the one or more fatty alcohols may include one or more of 2-propyl-heptanol, 2-butyl octanol, 2-pentyl-1-nonanol, 2-hexyl-1-decanol, 2-heptyl-1-undecanol, 2-octyl-1-dodecanol, 2-nonyl-1-tridecanol, 2-decyl-tetradecanol, 2-undecyl-1-pentadecanol, 2-dodecyl-hexadecanol, 2-tridecyl-heptadecanol, 2-tetradecyl-1-octadecanol, 2-pentadecyl-1-nonadecanol, 2-hexadecyl-1-eicosanol, 2-heptadecyl-1-heneicosanol, 2-octadecyl-1-docosanol, 2-nonadecyl-1-tricosanol, 2-eicosyl-tetracosanol, or combinations thereof. In an exemplary implementation, the one or more fatty alcohols includes 2-butyl octanol.

In at least one implementation, the one or more fatty alcohols may be present in an amount of from about 0.01 weight % to about 25 weight %, preferably about 0.01 weight % to about 5 weight %, more preferably in an amount of at least 0.16 weight % to about 5 weight %, or about 1.6 weight % to about 5 weight %, based on a total weight of the composition.

In at least one implementation, the one or more fatty alcohols are present in an amount effective to selectively inhibit the growth of detrimental bacteria, such as *Corynebacterium*. For example, one or more fatty alcohols are present in an amount effective to selectively inhibit the growth of *Corynebacterium striatum*.

In at least one implementation, the one or more fatty alcohols are present in an amount effective to selectively promote the growth of beneficial bacteria, such as *Staphylococcus*. For example the one or more fatty alcohols are present in an amount effective to selectively promote the growth of *S. epidermidis, S. haemolyticus*, or combinations thereof.

In at least one implementation, the composition may be a personal care composition. The personal care composition may be or include a cleanser, a lotion, a cream, an emulsion, a shampoo, a conditioner, a shower gel, an antiperspirant, a deodorant, a depilatory, a lipstick, a foundation, a mascara, a sunless tanner, or a sunscreen lotion.

In at least one implementation, the composition may include a deodorant active or an antiperspirant active.

The foregoing and/or other aspects and utilities embodied in the present disclosure may be achieved by providing a method for selectively treating the growth of a detrimental bacteria and promoting the growth of a beneficial bacteria on skin. The method may include contacting any one of the compositions disclosed herein with the skin.

In at least one implementation, the detrimental bacteria may include *Corynebacterium*.

In at least one implementation, the beneficial bacteria may include *Staphylococcus*.

In at least one implementation, the composition may be contacted with the skin daily for at least one week, at least two weeks, at least three weeks, or at least four weeks.

The foregoing and/or other aspects and utilities embodied in the present disclosure may be achieved by providing a method for producing or enhancing the production of antimicrobial peptides on skin. The method may include contacting any one of the compositions disclosed herein with the skin.

In at least one implementation, the method may further include promoting the growth of *Staphylococcus* on the skin to thereby produce or enhance the production of the antimicrobial peptides on the skin.

In at least one implementation, the composition may be contacted with the skin daily for at least one week, at least two weeks, at least three weeks, or at least four weeks.

The foregoing and/or other aspects and utilities embodied in the present disclosure may be achieved by providing a composition for use in treating or inhibiting the growth of a detrimental bacteria on skin. The composition may include a base and one or more fatty alcohols, wherein the one or more fatty alcohols are present in an amount effective to treat or inhibit the growth of the detrimental bacteria. The detrimental bacteria may include *Corynebacterium*.

The foregoing and/or other aspects and utilities embodied in the present disclosure may be achieved by providing a composition for use in promoting the growth of a beneficial bacteria on skin. The composition may include a base and one or more fatty alcohols, wherein the one or more fatty alcohols are present in an amount effective to promote the growth of the beneficial bacteria. The beneficial bacteria may include *Staphylococcus*.

The foregoing and/or other aspects and utilities embodied in the present disclosure may be achieved by providing a composition including a base and one or more fatty alcohols for use in selectively inhibiting the growth of at least one detrimental Gram-positive bacteria and promoting the growth of at least one beneficial Gram-positive bacteria on skin. The at least one detrimental Gram-positive bacteria may include *Corynebacterium*, optionally, *Corynebacterium striatum*. The at least one beneficial Gram-positive bacteria may include *Staphylococcus*, optionally, the *Staphylococcus* comprises *S. epidermidis, S. haemolyticus*, or combinations thereof.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that personal care compositions including one or more fatty alcohols, such as 2-butyl octanol, did not inhibit the growth of and/or promoted the growth of beneficial Gram-positive bacteria, such as *Staphylococcus* bacteria. The present inventors have also surprisingly and unexpectedly discovered that personal care compositions including one or more fatty alcohols, such as 2-butyl octanol, inhibit, treat, and/or reduce the growth of detrimental bacteria, such as *Corynebacterium*, especially when present in an amount of at least about 0.16 weight % or greater. The present inventors have further surprisingly and unexpectedly discovered that personal care compositions, such as deodorant or antiperspirant compositions, including one or more fatty alcohols, such as 2-butyl octanol, significantly and selectively reduced the relative abundance of detrimental bacteria (e.g., Corynebacteria) and increased the relative abundance of beneficial bacteria (e.g., *Staphylococcus*).

Compositions

Compositions disclosed herein may be or include a personal care composition. As used herein, the term or expression "personal care composition" may refer to a composition for topical application to skin of mammals, especially humans. The personal care composition may generally be a leave-on personal care composition or rinse off personal care composition, and may include any product applied to a human body. The personal care composition is preferably a leave-on personal care composition. The personal care composition may be in any suitable form. Illustrative forms of the personal care composition may be or include, but is not limited to, a liquid, a lotion, a cream, a foam, a scrub, a gel, a soap bar, a toner, applied with an implement or via a face mask, or the like. Illustrative personal care compositions may be or include, but are not limited to, cleansers, lotions, leave-on skin lotions and creams, emulsion, shampoos, conditioners, shower gels, antiperspirants, deodorants, depilatories, lipsticks, foundations, mascara, sunless tanners, sunscreen lotions, or the like.

In an exemplary implementation, the compositions disclosed herein may be or include an antiperspirant composition, a deodorant composition, or combinations thereof. The compositions may include a base, an antiperspirant and/or a deodorant active, one or more fatty alcohols (e.g., 2-butyl-1-octanol), or combinations thereof. The composition may be capable of or configured to treat, inhibit, and/or reduce detrimental bacteria on skin. The composition may be capable of treating, inhibiting, and/or reducing odor producing bacteria on skin, thereby reducing odor. The composition may also be capable of or configured to promote the growth of beneficial bacteria on skin. For example, as further described herein, the composition disclosed herein may be capable of or configured to treat, inhibit, and/or reduce the growth of *Corynebacterium* and/or promote the growth of *Staphylococcus* bacteria. The composition may further be capable of or configured to enhance or increase a barrier on the skin against colonization of potentially pathogenic microbes. For example, the composition may be capable of or configured to promote antimicrobial peptides (AMP) growth on the skin and provide a barrier against the colonization of potentially pathogenic microbes and the overgrowth of opportunistic pathogens on the skin.

The composition may be in the form of an aqueous liquid, a gel, an aerosol, or a cream (e.g., "soft solid"). In the liquid form, the composition may be formulated to be a roll-on product. In the liquid form, the composition may be an oil in water emulsion or a water in oil emulsion. The forms of these products may be suspensions or emulsions. In one implementation, the composition is an oil in water liquid emulsion. The liquid may be contained in any roll on dispenser that has a ball for applying the composition to the surface of the skin. For example, the composition of the invention may be an oil-in-water liquid roll-on or a water-in-oil gel or a water-in-oil cream.

Fatty Alcohols

The composition may include one or more fatty alcohols capable of or configured to treat, inhibit, and/or reduce detrimental bacteria. The one or more fatty alcohols may also be capable of or configured to promote the growth of beneficial bacteria on skin. For example, the one or more fatty alcohols may be capable of or configured to treat, inhibit, and/or reduce the growth of *Corynebacterium* and/or promote the growth of *Staphylococcus* bacteria. The fatty alcohols may be linear alcohols or branched alcohols. The fatty alcohols may be saturated or unsaturated. Illustrative fatty alcohols may be or include, but are not limited to, C10-C45 branched fatty alcohols, 2-propyl-heptanol, 2-butyl-1-octanol (2-butyl octanol), 2-pentyl-1-nonanol, 2-hexyl-1-decanol, 2-heptyl-1-undecanol, 2-octyl-1-dodecanol, 2-nonyl-1-tridecanol, 2-decyl-tetradecanol, 2-undecyl-1-pentadecanol, 2-dodecyl-hexadecanol, 2-tridecyl-heptadecanol, 2-tetradecyl-1-octadecanol, 2-pentadecyl-1-nonadecanol, 2-hexadecyl-1-eicosanol, 2-heptadecyl-1-heneicosanol, 2-octadecyl-1-docosanol, 2-nonadecyl-1-tricosanol, 2-eicosyl-tetracosanol, or the like, or any combination thereof. In an exemplary implementation, the one or more fatty alcohols include 2-butyl-1-octanol or 2-butyl octanol.

The one or more fatty alcohols may be present in an amount effective to treat, inhibit, and/or reduce detrimental bacteria on skin. The one or more fatty alcohols may also be present in an amount effective to treat, inhibit, and/or reduce odor producing bacteria on skin. The one or more fatty alcohols may further be present in an amount effective to promote the growth of beneficial bacteria on skin. The one or more fatty alcohols may also be present in an amount effective to enhance or increase a barrier on the skin against colonization of potentially pathogenic microbes. For example, the one or more fatty alcohols may be present in the composition in an amount effective to treat, inhibit, and/or reduce the growth of *Corynebacterium* and/or promote the growth of *Staphylococcus* bacteria. As used herein, an "effective amount," or similar expressions, of a material or composition may refer to the amount needed to accomplish an intended purpose; for example, to treat, inhibit, and/or reduce detrimental bacteria on skin.

In at least one implementation, the one or more fatty alcohols may be present in an amount of from greater than 0 weight % or about 0.01 weight % to about 25 weight %, based on a total weight of the composition. For example, the one or more fatty alcohols may be present in an amount of from greater than 0 weight %, about 0.01 weight %, about 0.02 weight %, about 0.04 weight %, about 0.08 weight %, about 0.16 weight %, about 0.20 weight %, about 0.25 weight %, about 0.5 weight %, about 0.75 weight %, about 1 weight %, about 1.6 weight %, about 2 weight %, about 5 weight %, about 8 weight %, or about 10 weight % to about 15 weight %, about 18 weight %, about 20 weight %, or about 25 weight %. In another exemplary implementation, the one or more fatty alcohols may be present in an amount of from about 0.01 weight % to about 25 weight % or about 0.01 weight % to about 5 weight %, based on a total weight of the composition. In another example, the one or more fatty alcohols may be present in an amount of at least 0.01 weight %, at least 0.02 weight %, at least 0.04 weight %, at least 0.08 weight %, at least 0.16 weight %, at least 0.20 weight %, at least 0.25 weight %, at least 0.5 weight %, at least 0.75 weight %, at least 1 weight %, at least 1.5 weight %, at least 1.6 weight %, at least 1.7 weight %, at least 1.8 weight %, at least 1.9 weight %, at least 2 weight %, at least 3 weight %, at least 4 weight %, at least 5 weight %, at least 8 weight %, at least 10 weight %, at least 15 weight %, at least 18 weight %, at least 20 weight %, or at least 25 weight %.

Antiperspirant Active

The composition may include an antiperspirant active. Any of the known aluminum containing antiperspirant active materials may be utilized in the composition. Illustrative antiperspirant actives may be or include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrate polyethylene glycol, aluminum sesquichlorohydrate propylene glycol, aluminum-zirconium octachlorohydrate, aluminum-zirconium octachlorohydrex gly, aluminum-zirconium pentachlorohydrate, aluminum-zirconium pentachlorohydrex gly, aluminum-zirconium tetrachlorohydrate, aluminum-zirconium tetrachlorohydrex gly, aluminum-zirconium trichlorohydrate, aluminum-zirconium trichlorohydrex gly, or the like, or any combination thereof. Generally, any of the Category I active antiperspirant ingredients, listed in the Food and Drug Administration's (FDA) Monograph on Antiperspirant Drug Products for over-the-counter human use (Oct. 10, 1973) may be used (21 CFR 350.10). In an exemplary implementation, the antiperspirant active is aluminum chlorohydrate. In another implementation, the antiperspirant active is aluminum zirconium tetrachlorhydrex propylene glycol.

In at least one implementation, the antiperspirant active may be an aluminum salt and/or an aluminum-zirconium salt, such as those described above, that are further stabilized by betaine and a calcium salt. More information betaine and calcium salt stabilized antiperspirant salts may be found in U.S. Patent Application Publication No. 2006/0204463 to Tang et al. In other implementations, the antiperspirant active, such as those described above, is selected to have a low metal to chloride ratio. Examples of these antiperspirant actives may be found in U.S. Pat. No. 6,375,937 to Chopra et al. and in U.S. Patent Application Publication No. 2004/0109833 to Tang et al. The type of salt of interest, an aluminum zirconium tetrasalt or octasalt free of glycine may be used wherein aluminum zirconium salt is stabilized by betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio may be about 3.2:1 to about 4.1:1.0 and the betaine:zirconium mole ratio may be about 0.2:1 to about 3.0:1 (or in other embodiments of about 0.4:1 to about 1.5:1). Another salt that may be used is an aluminum chloride salt buffered by betaine, wherein the salt has a metal to chloride ratio of about 0.9:1 to about 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the betaine:Zr mole ratio is about 0.2:1 to about 3.0:1 (or in other embodiments of about 0.4:1 to about 1.5:1). In one implementation, in the case of a salt that contains zirconium, the betaine is incorporated during the synthesis of the salt so as to maximize the stabilizing effect this ingredient has (especially on the zirconium species). Alternatively, it may be post added to a glycine-free salt along with additional active phase ingredients to form a betaine stabilized active. Additionally, the antiperspirant active may be a calcium salt stabilized antiperspirant active. Examples of calcium salt stabilized antiperspirant actives may be found in U.S. Patent Application Publication No. 2006/0204463.

Examples of commercially available glycine-free low M:Cl ratio tetrasalts and octasalts may be or include, but are not limited to, REZAL™ AZP 955 CPG and REZAL™ AZP 885 respectively, which are both commercially available from SummitReheis Antiperspirant Actives of Huguenot, NY A more detailed description of making such commercially available salts may be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

Antiperspirant actives may be incorporated into the compositions in an effective amount to reduce the flow or generation of perspiration when applied to skin. For example, the composition may include any one or more of the antiperspirant actives in an amount of from about 1 weight % to about 30 weight %, on an actives basis, based on a total weight of the composition.

Deodorant Active

The composition may include one or more deodorant actives. Illustrative deodorant actives may be or include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyltrimethylammomium bromide, cetyl pyridinium chloride, farnesol (3,7,11-trimethyl-2,6,10-dodecatrien-1-ol), N-(4-chlorophenyl)-N'-(3,4-dichlorophenyl)urea (Triclocarban), silver halides, octoxyglycerin (Sensiva™ SC 50) and various zinc salts (for example, zinc ricinoleate), bactericides, bacteriostats, or the like, or combinations thereof. The deodorant active may be present in an amount of from about 0 weight % to about 10 weight %, based on a total weight of the composition.

Base

As used herein, the term "base" may refer to or encompass all other materials in the composition that are not the antiperspirant active and/or the fatty alcohols. The base may provide or be capable of or configured to provide the form of the composition. As discussed above, the composition may be in the form of an aqueous liquid, a gel, an aerosol, or a cream. In at least one implementation, the composition is a solid stick or soft solid at ambient room temperature (e.g., about 25° C.). The stick form is an example of a solid form, and the soft solid is a thickened form that may or may not be solid. The stick form may be distinguished from a soft solid in that, in a stick, the formulated product may retain its shape for extended time periods outside the package, the product not losing its shape significantly (allowing for some shrinkage due to solvent evaporation). Adjustment of amounts of gelling or thickening agents may be used in order to form a soft solid or stick.

The compression force of a stick product may be greater than 3000 g. For example, the compression force of a stick product may be greater than 3000 g, greater than 4000 g, greater than 4500 g, greater than 5000 g, greater than 6000 g, greater than 7000 g, greater than 8000 g, or greater than 9000 g. In another implementation, the compression force may be from about 3500 g to about 10,000 g.

Gelling Agents

The composition may include one more gelling agents. Illustrative gelling agents may be or include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, other cosmetically acceptable materials, which are solid or semi solid at room temperature and provide a consistency suitable for application to the skin, or the like, or any combination thereof.

In at least one implementation, the gelling agent may include a combination of hydrogenated soybean oil and a hydrocarbon of the formula $C_nH_{2n+2}$, wherein n is 20 to 100, and the hydrocarbon is at least 90% linear. The fully or partially hydrogenated soybean oil may be or include those described in U.S. Patent Application Publication Nos. 2008/0187504A1 and 2008/0187503A1. The hydrogenated soybean oil from U.S. Patent Application Publication No. 2008/0187504A1 is almost, but not fully hydrogenated. The amount of hydrogenation is measured by the iodine value. The iodine value may be measured by ASTM D5554-95 (2006). The iodine value of the hydrogenated soybean oil used herein is greater than 0 to 20. The iodine value may be 1 to 5. The partially hydrogenated soybean oil from U.S. Patent Application Publication No. 2008/0187503A1 may have a melting point that of about −15° C. (5° F.) to 38° C. (100° F.). The melting point may alternatively be 26° C. (80° F.) to 38° C. (100° F.). To obtain the desired melting point, the oil may be partially hydrogenated or a blend of non-hydrogenated with partially or fully hydrogenated oils and/or waxes.

The partially or fully hydrogenated soybean oil may be present in an amount of from greater than 0 weight % to about 20 weight %, based on a total weight of the composition. In another example, the partially or fully hydrogenated soybean oil may be present in an amount of from greater than 0 to about 10 weight %, based on a total weight of the composition. In yet another example, the partially or fully hydrogenated soybean oil may be in an amount of at least 1 weight %, 2 weight %, 3 weight %, 4 weight %, 5 weight %, 6 weight %, 7 weight %, 8 weight %, or 9 weight %, based on the total weight of the composition. In another example, the amount may be present in an amount of less than 10 weight %, 9 weight %, 8 weight %, 7 weight %, 6 weight %, 5 weight %, 4 weight %, 3 weight %, 2 weight %, 1 weight %, based on a total weight of the composition.

As discussed above, the hydrocarbon may be a hydrocarbon of the formula $C_nH_{2n+2}$, where n is 20-100, and where the hydrocarbon may be at least 90% linear. In one example, the hydrocarbon may be or include a paraffin. In another example, the hydrocarbon may be or include polyethylene/polymethylene. The polyethylene may have a weight average molecular weight of from about 300 kDa to 3000 kDa. The polyethylene may have a melting point of from about 50° C. to about 129° C.

Volatile Silicone

The composition may include one or more volatile silicones. The volatile silicone may be a volatile cyclic polydimethylsiloxane (cyclomethicone), e.g., cyclopentasiloxane.

As used herein, the term volatile material or volatile silicone may refer to a material or silicone, respectively, that has a measurable vapor pressure at ambient temperature. Preferably, the volatile cyclic polydimethylsiloxane is cyclomethicone. Various types of cyclomethicones may be used. Illustratively, and not by way of limitation, the volatile silicones are one or more members selected from cyclic polydimethylsiloxanes such as those represented by Formula (I):

Formula (I)

where n may be an integer with a value of from 3 to 7, particularly from 5 to 6. Illustrative cyclomethicones may be or include, but are not limited to, DC-345 and DC-245, manufactured by Dow Corning Corporation of Midland, MI These types of cyclomethicones may include a tetramer (octylmethylcyclotetrasiloxane) and/or a pentamer (decamethylcyclopentasiloxane). The amount of any one or more of the volatile silicones present in the composition may be from about 5 weight % to about 70 weight %, based on a total weight of the composition. For example, the volatile silicones may be present in an amount of from about 25 weight % to about 45 weight %, based on a total weight of the composition.

The composition may include one or more ionizable inorganic salts. The ionizable salts may be in the form $M_aX_b$ where a=1, or 2 and b=1 or 2; M may be $Na^{+1}$, $Li^{+1}$, $K^{+1}$, $Mg^{+2}$, $Ca^{+2}$, $Sr^{+2}$, and $Zn^{+2}$, and X may be chloride, bromide, iodide, citrate, gluconate, lactate, glycinate, glutamate, ascorbate, aspartate, nitrate, phosphate, hydrogenphosphate, dihydrogenphosphate, formate, maloneate, maleate, succinate, carbonate, bicarbonate, sulfate, and hydrogensulfate. In some implementations, the salts are chosen from NaCl and $ZnCl_2$. As will be appreciated by those skilled in the art, while it may be possible under certain circumstances to add a salt directly to a portion of the mixture during manufacturing, it is desired to add the salt as a mixture or solution of the salt in a carrier or solvent, particularly water.

The composition may include one or more particulates. Illustrative particulates may be or include, but are not limited to, talc, mica, fragrance encapsulates, or hydrophobically modified starches, such as aluminum starch octenyl succinate (MACKADERM™ ASTRO-DRY™ commercially available from McIntyre Group Ltd. of University Park, IL.). If the composition is in a liquid form and dispensed through a roll-on applicator, the average particle size of the suspended material is sized so that it may pass through the application to prevent the ball applicator from malfunctioning. Usually, the average particle size does not exceed 150 microns.

The composition may include one or more optional ingredients, such as a malodor counteracting alpha, beta-unsaturated ester or mixtures of such materials. The level of the malodor counteracting composition to deliver a perceivable odor control benefit when delivered from an antiperspirant and/or deodorant composition may be from about 0.05 weight % to about 0.45 weight %, based on a total weight of the composition. The alpha, beta-unsaturated ester malodor counteracting materials may be incorporated within the oil phase of the composition. Example of these malodor counteracting components may be found in U.S. Pat. Nos. 6,610,648 and 6,495,097, the contents of which are incorporated herein only for their disclosure of the alpha, beta unsaturated esters. Examples of the alpha, beta unsaturated ester may be found in WO 2005/025523, which was filed in the U.S. as U.S. application Ser. No. 10/571,488, both of which are incorporated herein by reference to the extent that they do not conflict with the present disclosure.

Illustrative alpha, beta unsaturated esters may be or include, but are not limited to: (1) 3-phenyl-2-propenoic acid alkyl esters wherein $R^1$ is a substituent on the benzene ring and is chosen from an alkyl, an alkoxy, an aryl, or a substituted aryl. In certain embodiments, $R^1$ is chosen from H, a $C_1$ to $C_8$ alkyl, a $C_1$ to $C_8$ alkoxy, or an aryl; and $R^2$ is a subsistent group replacing the carboxylic acid hydrogen to form the ester where $R^2$ has greater than 6 carbon atoms, an aryl, or a substituted aryl group, in certain embodiments $R^2$ is a $C_6$ to $C_{12}$ alkyl or is a benzyl group; and (2) an ester of fumaric or maleic acid having linear ester carbon chains from 3-9 carbons, for example dihexyl fumarate; (3) e-phenyl propenoic acid ester chosen from octyl methoxy cinnamate, phenylethyl cinnamate, benzyl cinnamate; (4) an aliphatic unsaturated ester, such as dihexyl fumarate.

The composition may optionally include one or more absorbent materials. Illustrative absorbent materials may be or include, but are not limited to, corn starch, talc, clay, sodium polyacrylate, cotton fiber, fragrances, or the like, or combinations thereof.

When water is present, for example in a liquid roll-on composition, the water may make up the balance of the composition. In at least one implementation, the composition may include water in an amount of at least 20%, at least 30%, at least 40%, at least 50%, at least 60%, at least 70%, at least 80%, or at least 85%, based on a total weight of the composition.

As used herein, the "total solids of the composition" may refer to the amount of non-volatile materials in the composition. The percent solids is measured by a CEM Smart System moisture/solids analyzer which uses microwave energy to dry the samples. In one implementation, the total solids of the composition may be less than 30%, less than 25%, less than 20%, or less than 15%.

In aerosol form, any known and/or suitable aerosol propellant may be used.

The composition may include one or more antioxidants. Illustrative antioxidants may be or include, but are not limited to, butylated hydroxytoluene (BHT), pentaerythrityl tetra-di-t-butyl hydroxyhydrocinnamate (Tinogard TT™ from Ciba/BASF), caffeine, and *Abies picea* extract (GranLux™ AOX-G4 from Granula, which is a spruce knot extract in butylenes glycol).

The composition may include one or more emollients. The emollients may be present in an amount effective to achieve a desired emollient effect. It should be appreciated that emollients are known in the art and are used to impart a soothing effect on the skin.

Non-volatile emollients are preferable in the present invention. Classes of non-volatile emollients include non-silicone and silicone emollients. Non-volatile, non-silicone emollients include $C_{12-15}$ alkyl benzoate. The non-volatile silicone material may be a polyethersiloxane, polyalkyarylsiloxane or polyethersiloxane copolymer. An illustrative non-volatile silicone material may be or include, but is not limited to, phenyl trimethicone. Non-limiting examples of emollients may be found in U.S. Pat. No. 6,007,799. Illustrative emollients may be or include, but is not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide, or the like, or combinations thereof.

In at least one implementation, the one or more emollients may be or include, but are not limited to, linear silicones, cyclic silicones, hydrocarbons, polyhydroxy alcohols having more than 3 carbon atoms, liquid or solid polyalkyleneglycol ethers containing a polypropylene glycol (PPG) moiety and terminating in an alkyl ether, or the like, or combinations thereof. In another implementation, the emollient may be a volatile silicone, as discussed above, having a flash point of 100° C. or less, such as cyclomethicone, cyclopentasiloxane, or trisiloxane.

Surfactant

The compositions may include one or more surfactants. The one or more surfactants may be present in an amount of from greater than 0 weight % to about 20 weight %, based on a total weight of the composition. The one or more surfactants may be or include, but are not limited to anionic surfactants, cationic surfactants, amphoteric or zwitterionic surfactants, nonionic surfactants, silicone surfactants, or combinations thereof.

Illustrative nonionic surfactants may be or include, but are not limited to, (a) sorbitan esters and ethoxylated sorbitan esters (for example PEG-20 sorbitan isostearate, sorbitan monolaurate, polysorbate-20, polysorbate-40, polysorbate-60, polysorbate-80); (b) ethoxylates (for example, Ceteth-20, PEG-30 castor oil. PEG-40 hydrogenated castor oil, PEG-60 hydrogenated castor oil. Laureth-7, Isolaureth-6, Steareth-10. Steareth-20. Steareth-21, Steareth-100. Ceteareth-12, Oleth-5, Oleth-10); (c) ethoxylated adducts (for example, PEG-25 stearate, glyceryl stearate and PEG-100 stearate): (d) PEG esters (for example, PEG-8 oleate, PEG-8 laurate, PEG-8 dilaurate. PEG-12 dilaurate, PEG-80 diisostearate, PEG-40 stearate); (e) propoxylates (for example, PPG-10 butanediol, PPG-50 oleyl ether, PPG-2-ceteareth-9, PPG-3-deceth-3. PPG-5-ceteth-20); (f) ethoxylated modified triglycerides (for example, PEG-20 corn glycerides. PEG-12 palm kernel glycerides); (g) alkylphenol aromatic ethoxylates (for example, dinonylphenol ethoxylate with 9 moles of EO, octylphenol ethoxylate with 20 moles of EO, octylphenol ethoxylate with 40 moles of EO): (h) block copolymers that are alkoxylated glycols having ethoxylated and propoxylated segments (for example, POLOXAMER™ 182 and 234. POLOXAMER™ 105 Benzoate, and MEROXAPOL™ 174); or the like, or combinations thereof. In one implementation, the nonionic surfactant includes ethoxylated nonionic surfactants and propoxylated non-ionic surfactants. Example of these include, but are not limited to, Steareth 2, Steareth 20, and Steareth 21. In an oil in water composition, a combination of two surfactants, one having an HLB value of 2 to 8 (such as Steareth 2) and the other having an HLB of 9 to 18 (such as Steareth 20 and 21), may be used. In one implementation, the nonionic surfactant is selected such that it has an HLB (hydrophilic-lipophilic balance) value of from about 8 to about 16 or from about 8 to about 12.

Examples of silicone surfactants may be found in U.S. Pat. No. 6,485,716, which is incorporated herein by reference only for the listing of the silicone surfactants. Illustrative silicone surfactants may be or include, but are not limited to, silicone polyglucosides (for example, octyl dimethicone ethoxy glucoside) and silicone copolyols having an HLB (hydrophilic lipophilic balance) value of less than 8. The HLB value may be measured in a variety of ways such as described in conventional references or found listed in tables of data recording such values. It is intended that any type of HLB measurement technique may be used.

The silicone copolyols may include, but are not limited to, copolyols of the following Formula (II) and (III). Formula (II) materials may be represented by: $(R^{10})_3SiO[(R^{11})_2SiO]xSi(R^{12})(R^bO((C_2H_4O))_p(C_3H_6O)_s(R^c)O]_ySi(R^{13})$ wherein each of $R^{10}$, $R^{11}$, $R^{12}$, and $R^{13}$ may be the same or different and each is chosen from C1-C6 alkyl; $R^b$ is the radical $-C_mH2_m-$; $R^c$ is a terminating radical which may be hydrogen, an alkyl group of one to six carbon atoms, an ester group such as acyl, or an aryl group such as phenyl; m has a value of two to eight: p and s have values such that the oxyalkylene segment $-(C_2H_4O)_p-(C_3H_6O)_s-$ has a molecular weight in the range of 200 to 5,000; the segment preferably having 50 to 100 mole percent of oxyethylene units $-((C_2H_4O)_p-$ and 1 to 50 mole percent of oxypropylene units $-(C_3H_6O)_s-$; x has a value of 8 to 400; and y has a value of 2 to 40. Preferably each of $R^{10}$, $R^{11}$, $R^{12}$, and $R^{13}$ is a methyl group; $R^c$ is H; m is preferably three or four whereby the group $R^b$ is most preferably the radical $-(CH_2)_3-$; and the values of p and s are such as to provide a molecular weight of the oxyalkylene segment $-(C_2H_4O)_p-(C_3H_6O)_s-$ of between 1,000 to 3.000. In one embodiment, p and s should each have a value of 18 to 28. In a preferred implementation, the silicone copolyol is dimethicone copolyol. A second siloxane polyether (copolyol) may have the Formula (III): $(R^{10})_3Sio[(R^{11})_2SiO]xSi(R^{12})(R^bO(C_2H_4O)_pR^c)O]ySi(R^{13})_3$ wherein p has a value of 6 to 16; x has a value of 6 to 100; and y has a value of 1 to 20 and the other moieties have the same definition as defined in Formula (II).

It should be understood that in both Formulas (II) and (III) shown above, that the siloxane-oxyalkylene copolymers may, in alternate embodiments, take the form of end-blocked polyethers in which the linking group $R^b$, the oxyalkylene segments, and the terminating radical R occupy positions bonded to the ends of the siloxane chain, rather than being bonded to a silicon atom in the siloxane chain. Thus, one or more of the $R^{10}$, $R^{11}$, $R^{12}$, and $R^{13}$ substituents that are attached to the two terminal silicon atoms at the end of the siloxane chain may be substituted with the segment $-R^b-O-(C_2H_4O)_p-(C_3H_6O)_s-R^c$ or with the segment $-R^b-O-(C_2H_4O)-R^c$. In some instances, it may be desirable to provide the segment $-R^b-O-(C_2H_4O)_p-(C_3H_6O)_s-R^c$ or the segment $-R^b-O-(C_2H_4O)_p-R^c$ at locations which are in the siloxane chain as well as at locations at one or both of the siloxane chain ends.

Examples of suitable dimethicone copolyols are available either commercially or experimentally from a variety of suppliers including Dow Corning Corporation, Midland, MI; General Electric Company, Waterford, NY; Witco Corp., Greenwich, CT; and Goldschmidt Chemical Corporation, Hopewell, VA. Examples of products include DOW CORNING 5225C from Dow Corning, which is a 10% dimethicone copolyol in cyclomethicone; DOW CORNING 2-5185C, which is a 45-49% dimethicone copolyol in cyclomethicone; SILWET L-7622 from Witco; ABIL3 EM97 from Goldschmidt, which is an 85% dimethicone copolyol in D5 cyclomethicone; and various dimethicone copolyols available either commercially or in the literature.

It should also be noted that various concentrations of the dimethicone copolyols in cyclomethicone may be used. While a concentration of 10 weight % in cyclomethicone may often be seen commercially, other concentrations may be made by stripping off the cyclomethicone or adding additional cyclomethicone. The higher concentration materials such as DOW CORNING 2-5185 may be used in at least one implementation. In a preferred example, the silicone copolyol may be present in an amount of from about 0.5 weight % to about 5 weight %, or about 1 weight % to about 2 weight %, based on a total weight of the composition.

Illustrative anionic surfactants may also be or include, but are not limited to, sodium lauryl sulfate, sodium cocoyl monoglyceride sulfonate, sodium lauryl sarcosinate, sodium lauryl isoethionate, sodium laureth carboxylate, and sodium dodecyl benzenesulfonate.

Examples of zwitterionic surfactants include those which may be broadly described as derivatives of aliphatic quaternary ammonium, phosphonium, and sulfonium compounds, in which the aliphatic radicals may be straight chain or branched and wherein one of the aliphatic substituents contains from about 8 to 18 carbon atoms and one contains an anionic water-solubilizing group, e.g., carboxy, sulfonate, sulfate, phosphate, or phosphonate. Illustrative zwitterionic surfactants may be or include, but are not limited to 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P—P-diethyl-P-3,6,9trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methy-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)propane-1-phosphonate; 5-[N,N-di(3-hydroxypropyl)-N-hexadecylammonio]-2-hydroxy-pentane-1-sulfate; or the like, or combinations thereof.

Examples of amphoteric surfactants include those which may be broadly described as derivatives of aliphatic secondary and tertiary amines in which the aliphatic radical may be straight chain or branched and wherein one of the aliphatic substituents contains from 8 to 18 carbon atoms and one contains an anionic water solubilizing group, e.g., carboxy, sulfonate, sulfate, phosphate, or phosphonate. Examples of compounds falling within this definition are sodium 3-dodecylaminopropionate and sodium 3-dodecylaminopropane sulfonate. Further amphoteric surfactants are described in U.S. Pat. Nos. 2,658,072, 2,438,091 and 2,528,378.

The preferred amphoteric surfactants are betaines. Illustrative betaines useful herein may be or include, but are not limited to, the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxypropyl)carboxymethyl betaine, oleyl dimethyl gamma-carboxypropyl betaine, lauryl bis-(2-hydroxypropyl) alpha-carboxyethyl betaine, or the like, or combinations thereof. The sulfobetaines may be represented by coco dimethyl sulfopropyl betaine, stearyl dimethyl sulfopropyl betaine, amido betaines, amidosulfobetaines, or the like.

The compositions as disclosed herein are described and claimed with reference to their ingredients, as is usual in the art. As would be evident to one skilled in the art, ingredients may in some instances react with one another such that the true composition of the final formulation may not correspond exactly to the ingredients listed. As such, in some examples, it should be understood that the disclosure may extend to the product of the combination of the listed ingredients.

The compositions of the present disclosure may be manufactured using methods known in the art. Generally, the ingredients are combined and heated to melt the components (other than inert filler), and the melted components (together with particulate inert filler) are mixed. Desirably, volatile materials, such as the fragrance materials, are incorporated in the composition in the latter stages of the mixing cycle, in order to avoid volatilization thereof. After mixing, the molten composition may be poured directly into the dispensers, after which the compositions harden into a solid, and the container is capped to preserve the product until use.

As discussed above, the compositions disclosed herein may be applied to the skin of mammals. In an exemplary implementation, the compositions disclosed herein may be applied to the skin in the axillary area of a human.

Methods

The present disclosure may provide methods for treating, inhibiting, and/or reducing the growth of undesirable odor-causing bacteria on skin. For example, the present disclosure may provide methods for treating, inhibiting, and/or reducing the growth of *Corynebacterium*. The method may include applying or contacting any one of the compositions disclosed herein to the skin of the mammal. The method may also include applying or contacting any one of the compositions disclosed herein to the skin in the axillary area of the mammal. The method may also include administering any one of the compositions disclosed herein to the mammal in an amount effective to treat, inhibit, and/or reduce the growth of detrimental bacteria. The method may include applying or contacting any one of the compositions disclosed herein to the skin of the mammal at least once a day, at least two times a day, at least three times a day, or more. The method may include maintaining contact of the compositions disclosed herein to the skin for at least 1 hour, at least 3 hours, at least 5 hours, at least 10 hours, at least 15 hours, or at least 18 hours. The method may include applying or contacting any one of the compositions disclosed herein to the skin daily for at least 1 day, at least 2 days, at least 3 days, at least 4 days, at least 5 days, at least 6 days, at least 1 week, at least 2 weeks, at least 3 weeks, at least 4 weeks, at least 5 weeks, or more.

The present disclosure may also provide methods for reducing odor producing bacteria on skin. For example, the present disclosure may provide methods for treating, inhibiting, and/or reducing the amount of *Corynebacterium* on skin. The method may include applying or contacting any one of the compositions disclosed herein to the skin of the mammal. The method may also include applying or contacting any one of the compositions disclosed herein to the skin in the axillary area of the mammal. The method may also include administering any one of the compositions disclosed herein to the mammal in an amount effective to treat, inhibit, and/or reduce the amount of detrimental bacteria. The method may include applying or contacting any one of the compositions disclosed herein to the skin of the mammal at least once a day, at least two times a day, at least three times a day, or more. The method may include maintaining contact of the compositions disclosed herein to the skin for at least 1 hour, at least 3 hours, at least 5 hours, at least 10 hours, at least 15 hours, or at least 18 hours. The method may include applying or contacting any one of the compositions disclosed herein to the skin daily for at least 1 day, at least 2 days, at least 3 days, at least 4 days, at least 5 days, at least 6 days, at least 1 week, at least 2 weeks, at least 3 weeks, at least 4 weeks, at least 5 weeks, or more.

The present disclosure may also provide methods for promoting the growth of beneficial bacteria on skin. For example, the present disclosure may provide methods for promoting the growth of *Staphylococcus* bacteria. The method may include applying or contacting any one of the compositions disclosed herein to the skin of the mammal. The method may also include applying or contacting any one of the compositions disclosed herein to the skin in the axillary area of the mammal. The method may also include administering any one of the compositions disclosed herein to the mammal in an amount effective to promote the growth of beneficial bacteria. The method may include applying or contacting any one of the compositions disclosed herein to the skin of the mammal at least once a day, at least two times a day, at least three times a day, or more. The method may include maintaining contact of the compositions disclosed herein to the skin for at least 1 hour, at least 3 hours, at least 5 hours, at least 10 hours, at least 15 hours, or at least 18 hours. The method may include applying or contacting any one of the compositions disclosed herein to the skin daily for at least 1 day, at least 2 days, at least 3 days, at least 4 days, at least 5 days, at least 6 days, at least 1 week, at least 2 weeks, at least 3 weeks, at least 4 weeks, at least 5 weeks, or more.

The present disclosure may also provide methods for producing or enhancing the production of antimicrobial peptides on the skin. For example, the present disclosure may provide methods for promoting the growth of *Staphylococcus* bacteria, which produce antimicrobial peptides. The method may include applying or contacting any one of the compositions disclosed herein to the skin of the mammal to promote the growth of *Staphylococcus* bacteria. The method may also include applying or contacting any one of the compositions disclosed herein to the skin in the axillary area of the mammal. The method may also include administering any one of the compositions disclosed herein to the mammal in an amount effective to promote the growth of beneficial bacteria. The method may include applying or contacting any one of the compositions disclosed herein to the skin of the mammal at least once a day, at least two times a day, at least three times a day, or more. The method may include maintaining contact of the compositions disclosed herein to the skin for at least 1 hour, at least 3 hours, at least 5 hours, at least 10 hours, at least 15 hours, or at least 18 hours. The method may include applying or contacting any one of the compositions disclosed herein to the skin daily for at least 1 day, at least 2 days, at least 3 days, at least 4 days, at least 5 days, at least 6 days, at least 1 week, at least 2 weeks, at least 3 weeks, at least 4 weeks, at least 5 weeks, or more.

The present disclosure may also provide methods for providing, enhancing, or otherwise increasing a barrier on skin against the colonization of potentially pathogenic microbes. For example, the present disclosure may provide methods for promoting the growth of *Staphylococcus* bacteria, which provides or enhances the barrier against pathogenic microbes. The method may include applying or contacting any one of the compositions disclosed herein to the skin of the mammal to promote the growth of *Staphylococcus* bacteria. The method may also include applying or contacting any one of the compositions disclosed herein to the skin in the axillary area of the mammal. The method may also include administering any one of the compositions disclosed herein to the mammal in an amount effective to promote the growth of beneficial bacteria. The method may include applying or contacting any one of the compositions disclosed herein to the skin of the mammal at least once a day, at least two times a day, at least three times a day, or more. The method may include maintaining contact of the compositions disclosed herein to the skin for at least 1 hour, at least 3 hours, at least 5 hours, at least 10 hours, at least 15 hours, or at least 18 hours. The method may include applying or contacting any one of the compositions disclosed herein to the skin daily for at least 1 day, at least 2 days, at least 3 days, at least 4 days, at least 5 days, at least 6 days, at least 1 week, at least 2 weeks, at least 3 weeks, at least 4 weeks, at least 5 weeks, or more.

The present disclosure may provide methods for selectively treating, increasing, decreasing, promoting the growth of, and/or inhibiting the growth of one or more Gram-positive bacteria. Illustrative Gram-positive bacteria may be or include, but are not limited to, bacteria of the genera *Listeria, Staphylococcus, Streptococcus, Bacillus, Corynebacterium, Enterococcus, Peptostreptococcus, Clostridium*, or the like, or combinations thereof. Illustrative species may be or include, but are not limited to, *Listeria monocytogenes, Staphylococcus aureus* (including methicillin-resistant *S. aureus*, or MRSA), *Staphylococcus epidermidis, Streptococcus pyogenes, Streptococcus pneumoniae, Bacillus cereus, Staphylococcus haemolyticus, Staphylococcus epidermidis, Corynebacterium striatum, Bacillus anthracia, Clostridium botulinum, Clostridium perfringens, Clostridium difficile, Clostridium tetani, Corynebacterium diphtherias, Corynebacterium ulcerans, Enterococcus faecium* (including vancomycin-resistant *E. faecium*, or VRE), *Peptostreptococcus anaerobius*, or the like, or combinations thereof. The methods may include selectively treating, increasing, decreasing, promoting the growth of, and/or inhibiting the growth of one or more Gram-positive bacteria on skin in mammals. The method may include selectively increasing or promoting the growth of beneficial bacteria, such as *Staphylococcus*, while inhibiting or reducing the growth of detrimental bacteria, such as *Corynebacterium*. The method may include applying or contacting any one of the compositions disclosed herein to the skin of the mammal. The method may also include applying or contacting any one of the compositions disclosed herein to the skin in the axillary area of the mammal. The method may also include administering any one of the compositions disclosed herein to the mammal in an amount effective to selectively treat, decrease, promote the growth of, and/or inhibit the growth of one or more Gram-positive bacteria. The method may include applying or contacting any one of the compositions disclosed herein to the skin of the mammal at least once a day, at least two times a day, at least three times a day, or more. The method may include maintaining contact of the compositions disclosed herein to the skin for at least 1 hour, at least 3 hours, at least 5 hours, at least 10 hours, at least 15 hours, or at least 18 hours. The method may include applying or contacting any one of the compositions disclosed herein to the skin daily for at least 1 day, at least 2 days, at least 3 days, at least 4 days, at least 5 days, at least 6 days, at least 1 week, at least 2 weeks, at least 3 weeks, at least 4 weeks, at least 5 weeks, or more.

The present disclosure may provide a composition for use in treating, inhibiting, and/or reducing the growth of detrimental bacteria on skin. The composition may include a base, an antiperspirant and/or a deodorant active, one or more fatty alcohols (e.g., 2-butyl-1-octanol), or combinations thereof.

The present disclosure may provide a composition for use in reducing odor producing bacteria on skin. The composition may include a base, an antiperspirant and/or a deodorant active, one or more fatty alcohols (e.g., 2-butyl-1-octanol), or combinations thereof.

The present disclosure may provide a composition for use in promoting the growth of beneficial bacteria on skin. The composition may include a base, an antiperspirant and/or a deodorant active, one or more fatty alcohols (e.g., 2-butyl-1-octanol), or combinations thereof.

The present disclosure may provide a composition for use in producing or enhancing the production of antimicrobial peptides on the skin. The composition may include a base, an antiperspirant and/or a deodorant active, one or more fatty alcohols (e.g., 2-butyl-1-octanol), or combinations thereof.

The present disclosure may provide a composition for use in providing, enhancing, or otherwise increasing a barrier on skin against the colonization of potentially pathogenic microbes. The composition may include a base, an antiperspirant and/or a deodorant active, one or more fatty alcohols (e.g., 2-butyl-1-octanol), or combinations thereof.

As used herein, the expression or term "treating, inhibiting, and/or reducing bacterial growth" or similar expressions may refer to inhibition of the growth and/or reduction in the number of bacteria on a substrate (e.g., skin). Further, as used herein, the expression or term "promoting the growth of bacteria" or similar expressions may refer to the enhancement or increase in the rate of the growth of the bacteria without intervention, and/or increase in the number of bacteria on a substrate. The increase or decrease in the bacteria may be more than expected without intervention with the methods and/or compositions disclosed herein.

It should be appreciated that while implementations disclosed herein are generally directed to the treatment of humans, the compositions and methods disclosed herein may be equally applied to and performed on animal subjects, particularly mammalian subjects (e.g., mice, rats, dogs, cats, rabbits, horses, etc.), avian subjects (e.g., parrots, geese, quail, pheasant, etc.), livestock (e.g., pigs, sheep, goats, cows, chickens, turkey, duck, ostrich, emu, etc.), reptile and amphibian subjects.

All ingredients for use in the compositions described herein should be topically acceptable. As used herein, "topically acceptable" may refer to any ingredient that is present in a composition as described in an amount and form which does not render the composition unsafe for use on surfaces of skin.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The efficacy of 2-butyl octanol for selectively promoting, inhibiting, reducing, and/or treating bacterial growth was evaluated. Particularly, the efficacy of 2-butyl octanol for selectively promoting, inhibiting, reducing, and/or treating bacterial growth of *Corynebacterium* and *Staphylococcus* was evaluated. To evaluate the efficacy, an active solution was prepared by emulsifying 2-butyl octanol with a nonionic surfactant, namely, Polysorbate 80. The active solution included the 2-butyl octanol and the Polysorbate 80 in a ratio of about 83:17. Both positive controls (including no active solution) and negative controls (including no bacteria) were also prepared.

A 96-well plate was utilized to evaluate the growth of the respective bacteria at varying dilutions. Each of the wells of a 96-well plate was aseptically filled with about 100 μL of Tryptic Soy Broth (TSB). In the first well of each row, about 100 μL of either the active solution (including the 2-butyl octanol and Polysorbate 80) or the desired solvent for the respective positive and negative controls was added to thereby provide a total of about 200 μL in the first well of the each respective row. A multi-channel pipette was then utilized to prepare a two-fold dilution in each column. Specifically, a multi-channel pipette set to about 100 μL was utilized to mix and transfer about 100 μL of the 200 μL from the wells of the first column to the respective wells of a subsequent column. This was repeated for each of the remaining eleven columns. About 100 μL of the twelfth column was removed, thereby leaving about 100 μL in each of the 96 wells. For the negative control well, about 100 μL of a solvent that does not promote bacterial growth was added. Specifically, a phosphate buffered saline (PBS) was utilized for the negative control. About 100 μL of the respective bacteria adjusted to 0.1 optical density (OD) bacteria was added to all other wells. The well plate was then incubated overnight at about 37° C. in a growth inhibition assay machine. Measurements were taken at about one hour increments. The results of the analysis are summarized in Tables 1-3.

TABLE 1

Measured Optical Density of *S. Haemolyticus* with 2-Butyl Octanol

| Time | Concentration of 2-Butyl Octanol | | | | |
|---|---|---|---|---|---|
| (Hour) | 5.2% | 0.16% | 0.08% | 0.04% | 0.02% |
| 1 | 0.198 | 0.049 | 0.039 | 0.026 | 0.017 |
| 2 | 0.254 | 0.175 | 0.205 | 0.153 | 0.129 |
| 3 | 0.345 | 0.26 | 0.308 | 0.237 | 0.203 |
| 4 | 0.383 | 0.285 | 0.317 | 0.247 | 0.218 |
| 5 | 0.396 | 0.326 | 0.355 | 0.286 | 0.272 |
| 6 | 0.384 | 0.39 | 0.401 | 0.328 | 0.34 |
| 7 | 0.403 | 0.464 | 0.462 | 0.389 | 0.426 |
| 8 | 0.477 | 0.524 | 0.53 | 0.453 | 0.503 |
| 9 | 0.549 | 0.579 | 0.58 | 0.514 | 0.558 |
| 10 | 0.603 | 0.627 | 0.614 | 0.56 | 0.616 |
| 11 | 0.622 | 0.66 | 0.637 | 0.596 | 0.649 |
| 12 | 0.639 | 0.684 | 0.647 | 0.619 | 0.671 |
| 13 | 0.654 | 0.71 | 0.673 | 0.624 | 0.702 |
| 14 | 0.681 | 0.719 | 0.683 | 0.635 | 0.719 |

TABLE 1-continued

Measured Optical Density of S. Haemolyticus with 2-Butyl Octanol

| Time | Concentration of 2-Butyl Octanol | | | | |
|---|---|---|---|---|---|
| (Hour) | 5.2% | 0.16% | 0.08% | 0.04% | 0.02% |
| 15 | 0.699 | 0.724 | 0.693 | 0.656 | 0.724 |
| 16 | 0.722 | 0.74 | 0.708 | 0.657 | 0.735 |
| 17 | 0.742 | 0.756 | 0.733 | 0.671 | 0.748 |
| 18 | 0.752 | 0.77 | 0.744 | 0.676 | 0.751 |

TABLE 2

Measured Optical Density of S. Epidermidis with 2-Butyl Octanol

| Time | Concentration of 2-Butyl Octanol | | | | |
|---|---|---|---|---|---|
| (Hour) | 5.2% | 0.16% | 0.08% | 0.04% | 0.02% |
| 1 | 0.257 | 0.148 | 0.111 | 0.088 | 0.07 |
| 2 | 0.501 | 0.564 | 0.482 | 0.351 | 0.327 |
| 3 | 0.583 | 0.76 | 0.688 | 0.55 | 0.519 |
| 4 | 0.624 | 0.786 | 0.703 | 0.583 | 0.561 |
| 5 | 0.665 | 0.778 | 0.684 | 0.578 | 0.548 |
| 6 | 0.723 | 0.764 | 0.677 | 0.592 | 0.564 |
| 7 | 0.855 | 0.757 | 0.662 | 0.613 | 0.586 |
| 8 | 0.918 | 0.741 | 0.652 | 0.64 | 0.593 |
| 9 | 0.994 | 0.729 | 0.653 | 0.651 | 0.602 |
| 10 | 1.052 | 0.726 | 0.658 | 0.664 | 0.623 |
| 11 | 1.067 | 0.718 | 0.646 | 0.666 | 0.652 |
| 12 | 1.066 | 0.702 | 0.63 | 0.656 | 0.651 |
| 13 | 1.081 | 0.695 | 0.632 | 0.652 | 0.66 |
| 14 | 1.105 | 0.702 | 0.662 | 0.675 | 0.689 |
| 15 | 1.118 | 0.764 | 0.741 | 0.756 | 0.809 |
| 16 | 1.127 | 0.801 | 0.795 | 0.825 | 0.893 |
| 17 | 1.142 | 0.844 | 0.883 | 0.915 | 0.951 |
| 18 | 1.127 | 0.874 | 0.943 | 0.961 | 0.97 |

TABLE 3

Measured Optical Density of C. Striatum with 2-Butyl Octanol

| Time | Concentration of 2-Butyl Octanol | | | |
|---|---|---|---|---|
| (Hour) | 0.16% | 0.08% | 0.04% | 0.02% |
| 1 | 0.038 | 0.014 | 0.006 | 0 |
| 2 | 0.037 | 0.07 | 0.058 | 0.086 |
| 3 | 0.036 | 0.108 | 0.088 | 0.13 |
| 4 | 0.036 | 0.118 | 0.1 | 0.139 |
| 5 | 0.036 | 0.124 | 0.111 | 0.143 |
| 6 | 0.036 | 0.127 | 0.117 | 0.144 |
| 7 | 0.035 | 0.129 | 0.121 | 0.144 |
| 8 | 0.036 | 0.131 | 0.124 | 0.144 |
| 9 | 0.036 | 0.132 | 0.127 | 0.146 |
| 10 | 0.037 | 0.133 | 0.13 | 0.149 |
| 11 | 0.037 | 0.133 | 0.133 | 0.155 |
| 12 | 0.037 | 0.134 | 0.136 | 0.163 |
| 13 | 0.038 | 0.137 | 0.141 | 0.178 |
| 14 | 0.038 | 0.141 | 0.149 | 0.21 |
| 15 | 0.039 | 0.151 | 0.166 | 0.254 |
| 16 | 0.04 | 0.168 | 0.192 | 0.322 |
| 17 | 0.041 | 0.194 | 0.234 | 0.404 |
| 18 | 0.041 | 0.23 | 0.298 | 0.52 |

As indicated in Tables 1-3, the 2-butyl octanol selectively or preferably inhibited the bacterial growth of Corynebacterium and promoted the growth of Staphylococcus. Specifically, the presence of 2-butyl octanol, surprisingly and unexpectedly, did not inhibit the growth of and/or promoted the growth of S. epidermidis and S. hominis when present in an amount of about 0.02 weight % to about 5.2 weight %. Conversely, when 2-butyl octanol was present in an amount of at least about 1.6% or greater the growth of C. stratium was completely inhibited (Table 3). It should be appreciated that amounts of 2-butyl octanol greater than about 5.2 weight were not measured as the system because too turbid to be measured.

Example 2

The efficacy of 2-butyl octanol in a personal care composition for selectively promoting, inhibiting, reducing, and/or treating bacterial growth was evaluated. Particularly, a control or base deodorant composition (1) and a test deodorant composition including 2-butyl octanol were prepared by combining the ingredients/components according to Table 4. The control (1) and test (2) deodorant compositions were evaluated in an in-house panel study with 11 subjects. Each of the subjects used the control (1) and test (2) deodorant compositions once daily for four weeks. Specifically, each of the subjects used the control deodorant composition (1) in one underarm and the test deodorant composition (2) in the other underarm. After four weeks of daily usage, samples were collected from the underarm and bacteria genomic analysis (16S rRNA sequencing) was performed on these samples. The results of the evaluation are summarized in Table 5.

TABLE 4

Control (1) and Test (2) Deodorant Compositions Weight (%)

| COMPONENT | 1 | 2 |
|---|---|---|
| Water | 79.90 | 76.90 |
| Emollients | 6.00 | 6.00 |
| Surfactants | 6.5 | 6.5 |
| Preservative | 0.40 | 0.40 |
| Excipients | Balance | Balance |
| 2-Butyl octanol | 0.0 | 3.0 |

TABLE 5

Relative Abundance of Bacteria (%) Before and After Treatment with Control (1) and Test (2) Deodorant Compositions

| COMPONENT | (1) Initial | (1) 4 Weeks | (2) Initial | (2) 4 Weeks |
|---|---|---|---|---|
| Cornybacterium | 29.30 | 20.42 | 42.47 | 13.34 |
| Staphylococcus | 44.72 | 37.09 | 36.22 | 58.85 |

As indicated in Table 5, the test deodorant composition (2) including the 2-butyl octanol surprisingly and unexpectedly exhibited a significant reduction in the relative abundance of Corynebacteria from about 42% to about 13% (p=0.004) and increased the relative abundance of Staphylococcus from about 36% to about 59% (p=0.02). The results are both surprising and unexpected, as the control deodorant composition (1) decreased the relative abundances of both the Corynebacteria and Staphylococcus bacteria.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A composition comprising:
a base;
one or more deodorant actives;
one or more nonionic surfactants;
wherein the one or more nonionic surfactants are selected from the group consisting of ethoxylated nonionic surfactants, propoxylated nonionic surfactants, and a combination thereof; and
wherein the ethoxylated nonionic surfactant is Steareth 2; and
a fatty alcohol;
wherein the fatty alcohol comprises 2-butyl octanol;
wherein the fatty alcohol is present in an amount of about 0.20 weight %, based on a total weight of the composition; and
wherein the fatty alcohol is present in an amount effective to selectively inhibit the growth of *Corynebacterium striatum* and promote the growth of at least one beneficial Gram-positive bacteria on skin.

2. The composition of claim 1, wherein the at least one beneficial Gram-positive bacteria comprises *Staphylococcus*, optionally, the *Staphylococcus* comprises *S. epidermidis, S. haemolyticus*, or combinations thereof.

3. The composition of claim 1, wherein the composition is a personal care composition, preferably the personal care composition is a cleanser, a lotion, a cream, an emulsion, a shampoo, a conditioner, a shower gel, an antiperspirant, a deodorant, a depilatory, a lipstick, a foundation, a mascara, a sunless tanner, or a sunscreen lotion.

4. The composition of claim 1, wherein the deodorant active is selected from one or more of the group consisting of benzethonium chloride, polyhexamethylene biguanides, triethylcitrate, 2-amino-2-methyl-1-propanol (AMP), cetyltrimethylammomium bromide, cetyl pyridinium chloride, farnesol (3,7,11-trimethyl-2,6,10-dodecatrien-1-ol), N-(4-chlorophenyl)-N'-(3,4-dichlorophenyl) urea (Triclocarban), silver halides, octoxyglycerin, and zinc salts, bactericides, bacteriostats, or combinations thereof, and
wherein the zinc salt is zinc ricinoleate.

5. The composition of claim 4, wherein the deodorant active is present in an amount from about 0 weight % to about 10 weight %, based on a total weight of the composition.

6. A method for selectively treating the growth of a detrimental bacteria and promoting the growth of a beneficial bacteria on skin, the method comprising contacting the composition of claim 1 with the skin, wherein the detrimental bacteria comprises *Corynebacterium*.

7. The method of claim 6, wherein the beneficial bacteria comprises *Staphylococcus*.

8. The method of claim 6, wherein the composition is contacted with the skin daily for at least one week, at least two weeks, at least three weeks, or at least four weeks.

9. A method for reducing odor producing bacteria on skin, the method comprising contacting the composition of claim 1 with the skin, optionally, wherein the odor producing bacteria comprises *Corynebacterium*.

10. The composition of claim 1 for use in treating or inhibiting the growth of a detrimental bacteria on skin, optionally, the detrimental bacteria comprises *Corynebacterium*.

11. The composition of claim 1 for use in promoting the growth of a beneficial bacteria on skin, optionally, the beneficial bacteria comprises *Staphylococcus*.

12. A composition comprising:
a base;
one or more nonionic surfactants;
wherein the one or more nonionic surfactants are selected from the group consisting of ethoxylated nonionic surfactants, propoxylated nonionic surfactants, and a combination thereof; and
wherein the ethoxylated nonionic surfactant is Steareth 2; and
a fatty alcohol comprising 2-butyl octanol,
wherein the fatty alcohol is present in an amount of about 0.20 weight %, based on a total weight of the composition; and
wherein the fatty alcohol is present in an amount effective to selectively inhibit the growth of *Corynebacterium striatum* and promote the growth of at least one beneficial Gram-positive bacteria on skin.

13. The composition of claim 1, wherein the one or more nonionic surfactants selected from the group consisting of ethoxylated nonionic surfactants and propoxylated nonionic surfactants are further selected from Steareth 20.

* * * * *